(12) United States Patent (10) Patent No.: US 9,113,895 B2
McEwen et al. (45) Date of Patent: Aug. 25, 2015

(54) INTEGRATED TOURNIQUET SYSTEM

(75) Inventors: James A. McEwen, Vancouver (CA); Michael Jameson, North Vancouver (CA); Michael A. Gebert, New Westminister (CA); William K. W. Cheung, Vancouver (CA)

(73) Assignee: Western Clinical Engineering Ltd., Vancouver, British Columbia (CA)

( * ) Notice: Subject to any disclaimer, the term of this patent is extended or adjusted under 35 U.S.C. 154(b) by 1830 days.

(21) Appl. No.: 12/389,029

(22) Filed: Feb. 19, 2009

(65) Prior Publication Data

US 2010/0211096 A1 Aug. 19, 2010

(51) Int. Cl.
*A61B 17/00* (2006.01)
*A61B 17/135* (2006.01)
*A61B 19/00* (2006.01)

(52) U.S. Cl.
CPC ... *A61B 17/1355* (2013.01); *A61B 2017/00119* (2013.01); *A61B 2017/00132* (2013.01); *A61B 2017/00221* (2013.01); *A61B 2019/4847* (2013.01)

(58) Field of Classification Search
CPC .............. A61B 17/1355; A61B 2017/00132; A61B 2017/00137; A61B 17/135; A61B 17/132; A61B 17/1322; A61B 17/1325; A61F 5/02; A61F 5/021; A61F 5/0205; A61F 5/02141; A61F 5/022; A61F 5/02208; A61F 5/02216; A61F 5/02225; A61F 5/02233; A61F 5/02241; A61F 5/0225; A61F 5/0235; A61F 5/024
USPC ................................................ 606/202, 203
See application file for complete search history.

(56) References Cited

U.S. PATENT DOCUMENTS

| | | | |
|---|---|---|---|
| 4,321,929 A | 3/1982 | Lemelson | |
| 4,469,099 A | 9/1984 | McEwen | |
| 4,479,494 A | 10/1984 | McEwen | |
| 4,548,198 A | 10/1985 | Manes | |
| 4,605,010 A | 8/1986 | McEwen | |
| 4,635,635 A | 1/1987 | Robinette-Lehman | |
| 4,671,290 A | 6/1987 | Miller | |
| 4,869,265 A | 9/1989 | McEwen | |
| 5,048,536 A | 9/1991 | McEwen | |
| 5,181,522 A | 1/1993 | McEwen | |
| 5,254,087 A | 10/1993 | McEwen | |
| 5,307,791 A * | 5/1994 | Senoue et al. ................ 601/150 |
| 5,312,431 A | 5/1994 | McEwen | |

(Continued)

FOREIGN PATENT DOCUMENTS

WO 0197747 12/2001

OTHER PUBLICATIONS

International Search Report and Written Opinion, related application No. PCT/CA2010/000175, 11 pages; May 12, 2010.

(Continued)

*Primary Examiner* — Katherine Rodjom
*Assistant Examiner* — Kendra Obu
(74) *Attorney, Agent, or Firm* — Klarquist Sparkman, LLP

(57) ABSTRACT

An integrated tourniquet system enables the user to establish with suitable warnings, and with timely user confirmation, individualized maximum pressure levels in the cuff that may be above normal maximum pressure levels. Also provided is a rapid and accurate method of testing for leakage in the cuff and connectors. The system is adapted for communication to remote devices for receiving and providing information relating to the pressure levels, tests, etc.

21 Claims, 4 Drawing Sheets

(56) References Cited

U.S. PATENT DOCUMENTS

| | | |
|---|---|---|
| 5,439,477 A | 8/1995 | McEwen |
| 5,454,831 A | 10/1995 | McEwen |
| 5,556,415 A | 9/1996 | McEwen |
| 5,569,304 A | 10/1996 | Ulrich |
| 5,578,055 A | 11/1996 | McEwen |
| 5,584,853 A | 12/1996 | McEwen |
| 5,607,447 A | 3/1997 | McEwen |
| 5,649,954 A | 7/1997 | McEwen |
| 5,681,339 A | 10/1997 | McEwen |
| 5,741,295 A | 4/1998 | McEwen |
| 5,855,589 A | 1/1999 | McEwen |
| 5,911,735 A | 6/1999 | McEwen |
| 5,935,146 A | 8/1999 | McEwen |
| 5,951,502 A | 9/1999 | Peeler |
| 6,051,016 A | 4/2000 | Mesaros |
| 6,213,939 B1 | 4/2001 | McEwen |
| 6,371,937 B1 | 4/2002 | McPhee |
| 6,475,228 B1 | 11/2002 | Mesaros |
| 6,589,268 B1 | 7/2003 | McEwen |
| 6,605,103 B2 | 8/2003 | Hovanes |
| 6,682,547 B2 | 1/2004 | McEwen |
| 6,736,787 B1 * | 5/2004 | McEwen et al. ............. 601/152 |
| 7,331,977 B2 | 2/2008 | McEwen |
| 7,479,154 B2 | 1/2009 | McEwen |
| 2003/0036771 A1 | 2/2003 | McEwen |
| 2003/0126912 A1 | 7/2003 | Cook |
| 2003/0167070 A1 | 9/2003 | McEwen |
| 2003/0236548 A1 | 12/2003 | Hovanes |
| 2004/0147956 A1 | 7/2004 | Hovanes |
| 2006/0224181 A1 * | 10/2006 | McEwen et al. ............. 606/202 |
| 2006/0253150 A1 | 11/2006 | McEwen |
| 2006/0287672 A1 | 12/2006 | McEwen |
| 2007/0032818 A1 | 2/2007 | McEwen |
| 2007/0032819 A1 | 2/2007 | McEwen |
| 2007/0255310 A1 | 11/2007 | Hovanes |
| 2008/0262533 A1 | 10/2008 | McEwen |
| 2009/0124912 A1 * | 5/2009 | McEwen et al. ............. 600/495 |
| 2009/0240191 A1 * | 9/2009 | Loori et al. ............. 604/23 |
| 2010/0204726 A1 | 8/2010 | McEwen |
| 2010/0211096 A1 | 8/2010 | McEwen |

OTHER PUBLICATIONS

AORN Standards, Recommended Practices, and Guidelines, 2007 Edition; Recommended Practices for the Use of the Pneumatic Tourniquet in the Perioperative Practice Setting; circa Jan. 1, 2007; pp. 617-629.

Extended European Search Report; issued Mar. 3, 2014 in corresponding EP Application No. 10743353.4, 9 pages.

* cited by examiner

INTEGRATED TOURNIQUET SYSTEM

FIELD OF THE INVENTION

This invention pertains to pneumatic tourniquet systems commonly used for stopping the flow of arterial blood into a portion of a surgical patient's limb to facilitate the performance of a surgical procedure and for facilitating intravenous regional anesthesia.

BACKGROUND OF THE INVENTION

Surgical tourniquet systems are commonly used to stop the flow of arterial blood into a portion of a patient's limb, thus creating a clear, dry surgical field that facilitates the performance of a surgical procedure and improves outcomes. A typical surgical tourniquet system of the prior art includes a tourniquet cuff for encircling a patient's limb at a desired location, a tourniquet instrument, and flexible pneumatic tubing connecting the cuff to the instrument. In some surgical tourniquet systems of the prior art, the tourniquet cuff includes an inflatable portion, and the inflatable portion of the cuff is connected pneumatically through flexible plastic tubing and one or more connectors to a tourniquet instrument.

A typical tourniquet instrument of the prior art includes a pressure regulator to maintain the pressure in the inflatable portion of the cuff, when applied to a patient's limb at a desired location, near a reference pressure level that is above a minimum pressure required to stop arterial blood flow past the cuff during a time period suitably long for the performance of a surgical procedure. The reference pressure level may be set manually by a user, it may be determined automatically for an individual patient, or it may adapt automatically during a surgical procedure. Many types of such pneumatic surgical tourniquet systems have been described in the prior art, such as those described by McEwen in U.S. Pat. No. 4,469,099, No. 4,479,494, No. 5,439,477 and by McEwen et al in U.S. Pat. No. 5,607,447, No. 5,855,589 and No. 7,479,154.

Tourniquet instruments known in the prior art are not fully integrated with the tourniquet cuffs connected to them, or with ancillary apparatus in the operating room. As a result, typical prior-art tourniquet systems cannot change their operation in ways that could significantly improve their safety, performance and reliability.

The earliest surgical tourniquet systems of the prior art were entirely mechanical and thus had no integration or connectivity with other apparatus in the operating room. The invention and introduction into practice of the first surgical tourniquets employing digital technology, as described by McEwen in U.S. Pat. No. 4,469,099, enabled their integration with other apparatus in the surgical suite and with digital operating-room information systems. For example, in U.S. Pat. No. 4,479,494 McEwen describes a tourniquet system communicating with apparatus monitoring the surgical patient's blood pressure, thereby allowing the tourniquet system to receive blood pressure information and adapt tourniquet cuff pressure accordingly, and communicating with a separate printer to remotely record and display information relating to tourniquet operation. Ulrich in U.S. Pat. No. 5,569,304 describes tourniquet apparatus communicating with automatic blood pressure measuring apparatus. As another example, in U.S. Pat. No. 5,607,447 McEwen and Jameson describe a tourniquet system having an internal event register for storing certain predetermined events relating to tourniquet usage, and including connectivity allowing the recording and display of the stored events by a remote printer.

Typically, surgical tourniquet systems of the prior art have included means for enabling tourniquet cuff pressure to be set to levels of pressure that do not exceed a maximum limit. The earliest prior-art tourniquet systems often had maximum limits determined by the apparatus itself, for example by the maximum limit of the specific pressure regulator employed or by the maximum pressure of the source of gas supplying the pressure regulator. In one such system known in the prior art, the maximum limit that could be set by a user was 1000 mmHg.

Evidence from many studies published in the medical literature over the years has demonstrated that higher tourniquet pressures are associated with higher probabilities of patient injuries. Following the introduction of digital tourniquet systems such as those described by McEwen in U.S. Pat. No. 4,469,099, their increased accuracy, reliability and safety allowed users to routinely set lower and safer maximum limits in tourniquet systems based on patient safety considerations. For some prior-art surgical tourniquet systems that are widely used at present, the maximum limit is 475 mmHg. The lower maximum limit is intended to help prevent inadvertent or unintentional setting of tourniquet cuff pressure to hazardous levels higher than needed to stop arterial blood flow for the duration of a surgical procedure. A predetermined maximum limit of tourniquet pressure based on patient safety has proven to be satisfactory for almost all normal adult patients undergoing surgery in normal limbs that are encircled by standard tourniquet cuffs.

However, for some surgical patients, limbs and situations, the predetermined maximum limit to which pressure can be set in known prior-art tourniquet systems may be insufficient to stop arterial blood flow and thus establish a bloodless field to facilitate surgery. Examples include: patients who are very obese; patients who have certain abnormal medical conditions such as hypertension; patients who have abnormal physiology or anatomy, including calcified arterial vessels or limbs of large circumference; and situations where certain non-standard types of tourniquet cuffs are used. Alternatively, for some patients and limbs and situations, the predetermined maximum limit of known prior-art tourniquet systems may be much higher than required to stop blood flow, and thus may allow tourniquet pressure to be set to levels that are unnecessarily and hazardously high. For example, lower tourniquet pressure settings are typically sufficient and safer for many pediatric patients, for adult patients who are of small physical size or who have limbs of small circumference, and when tourniquet cuffs having variable-contour shapes and greater widths are employed.

Leakage of pressurized gas from the tourniquet cuff, from pneumatic tubing between the instrument and cuff, and from connectors that attach the tubing to the cuff and instrument may affect tourniquet safety, performance, and reliability. Accordingly, the 2007 Recommended Practices for the Use of the Pneumatic Tourniquet in the Perioperative Practice Setting (RPs) of the US Association of periOperative Nurses (AORN) recommend that the tourniquet cuff, tubing, and connectors should be kept clean and in good working order. The AORN RPs further recommend, based on published literature, that the tourniquet cuff, tubing and connectors should be inspected for cracks and leaks because unintentional pressure loss can result from loose tubing connectors, deteriorated tubing, or cuff bladder leaks, and may result in patient injury. At present, because tourniquet systems of the prior art are not fully integrated with the cuffs connected to them through tubing and connectors, such inspections and checking are performed manually and often inconsistently, or only after a hazardous incident or patient injury has occurred.

To best comply with the 2007 AORN Recommended Practices regarding inspection and checking of tourniquet cuffs, connectors, and tubing, their pneumatic integrity should be routinely checked between surgical procedures and surgical staff should be alerted to any potential hazards found so that remedial action can be taken promptly. If this is not done, then leaking and potentially hazardous tourniquet cuffs, connectors, and tubing may be used for surgery, and may remain in use for long periods of time. Also, users may not be alerted to defects which may be small initially but which may increase to become significant hazards for patients, either slowly or very rapidly. Additionally, unauthorized reprocessing and reuse of cuffs manufactured to be single-use disposable cuffs may introduce leakage hazards if such cuffs are not carefully inspected before each reuse, or after each reuse, because improper, uncontrolled and unlimited reprocessing may impair the shape and integrity of the pneumatic seals of cuff connectors. Even if disposable tourniquet cuffs are used as single-use products, and if it is assumed that such cuffs are not leaking at time of first use, the tubing and connectors that connect the disposable cuffs to the tourniquet instrument may leak and such leakage may go undetected, allowing the leaking tubing or connectors to remain in use until an obvious patient hazard or injury occurs, and during which time other limitations in tourniquet safety, performance and reliability are produced.

Pneumatic leakage in tourniquet systems that is not detected by routine inspections and checking is undesirable in surgery and may be hazardous. In the past, undetected pneumatic leakage led users of prior-art systems to set tourniquet pressures at reference levels that were substantially higher than required physiologically to compensate for intra-operative reductions in cuff pressure that users had observed but had not been able to attribute to obvious leakage. However, setting unnecessarily high pressures is hazardous because in the medical literature higher tourniquet pressure levels have been associated with higher probabilities of patient injuries to nerves and soft tissues. More recently, some surgical tourniquet systems of the prior art have attempted to compensate for undetected levels of pneumatic leakage in the design of their pressure regulators. In typical systems, the pressure regulator is designed to maintain cuff pressure within a predetermined pressure range from a reference pressure, and any fluctuations beyond that range are offset by actuation of a pump, reservoir, or valve in an effort to bring the cuff pressure back within the range. If there is pneumatic leakage sufficient to cause the cuff pressure to decrease beyond the predetermined pressure range, actuation of the pressure regulator may bring it back within range, and if not a pressure-regulation alarm is produced. Such systems of the prior art may compensate for significant levels of sustained, undetected leakage without producing any indication of leakage or alarm for the user. Further, sustained leakage may produce an error in the indicated tourniquet cuff pressure in single-port tourniquet systems of the prior-art which estimate cuff pressure by measuring pneumatic pressure within the tourniquet instrument. For typical surgical tourniquet systems of the prior art, three limitations in the performance and reliability of their pressure regulators exist in the presence of undetected pneumatic leakage. First, tourniquet cuff pressure fluctuates unnecessarily as decreases in cuff pressure are offset by the actuations of the pressure regulator. Second, unnecessarily frequent actuation of the pressure regulator reduces the operational life and reliability of its mechanical components, increases the cost of maintaining and replacing those components, and may increase capital costs by necessitating early replacement of the entire tourniquet instrument. Third, operation of prior-art tourniquet systems on battery power is impaired. Typical tourniquet systems of the prior art may be powered either by external AC power or by an internal battery, so that they can continue to operate safely in the event of a sudden interruption of external power, and so that they can operate independently of external AC power for a prolonged period of time, for example during transportation of a patient from a pre-operative room to the operating room, or to facilitate surgery under emergency or battlefield conditions. However, in the presence of sustained leakage pneumatic leakage, the operational time of a tourniquet system when powered by an internal battery for surgery may be substantially reduced due to unnecessary actuations of the pressure regulator. Additionally, the overall life of the internal battery may be significantly reduced, reducing the performance and reliability of the tourniquet system and thereby increasing costs and hazards.

There is a need for a surgical tourniquet system that overcomes the above-described limitations of the prior art. For example, no system is known in the prior art that prevents the inadvertent or unintentional setting of tourniquet pressure to a level substantially higher than needed for one individual surgical patient, and yet allows such high pressure levels to be set if needed to stop blood flow in another individual patient. As another example, no tourniquet system known in the prior art includes means for automatically checking the integrity of its pneumatic components prior to each use, or after each use, or for identifying, recording and alerting the user to possible hazards identified by such checking. As yet another example, no known prior-art tourniquet system communicates information about the results of such pneumatic integrity checking, or information on individualized maximum pressure limits, to a remote display, printer or other apparatus to inform the user, to record the information for quality assurance, or for other purposes.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
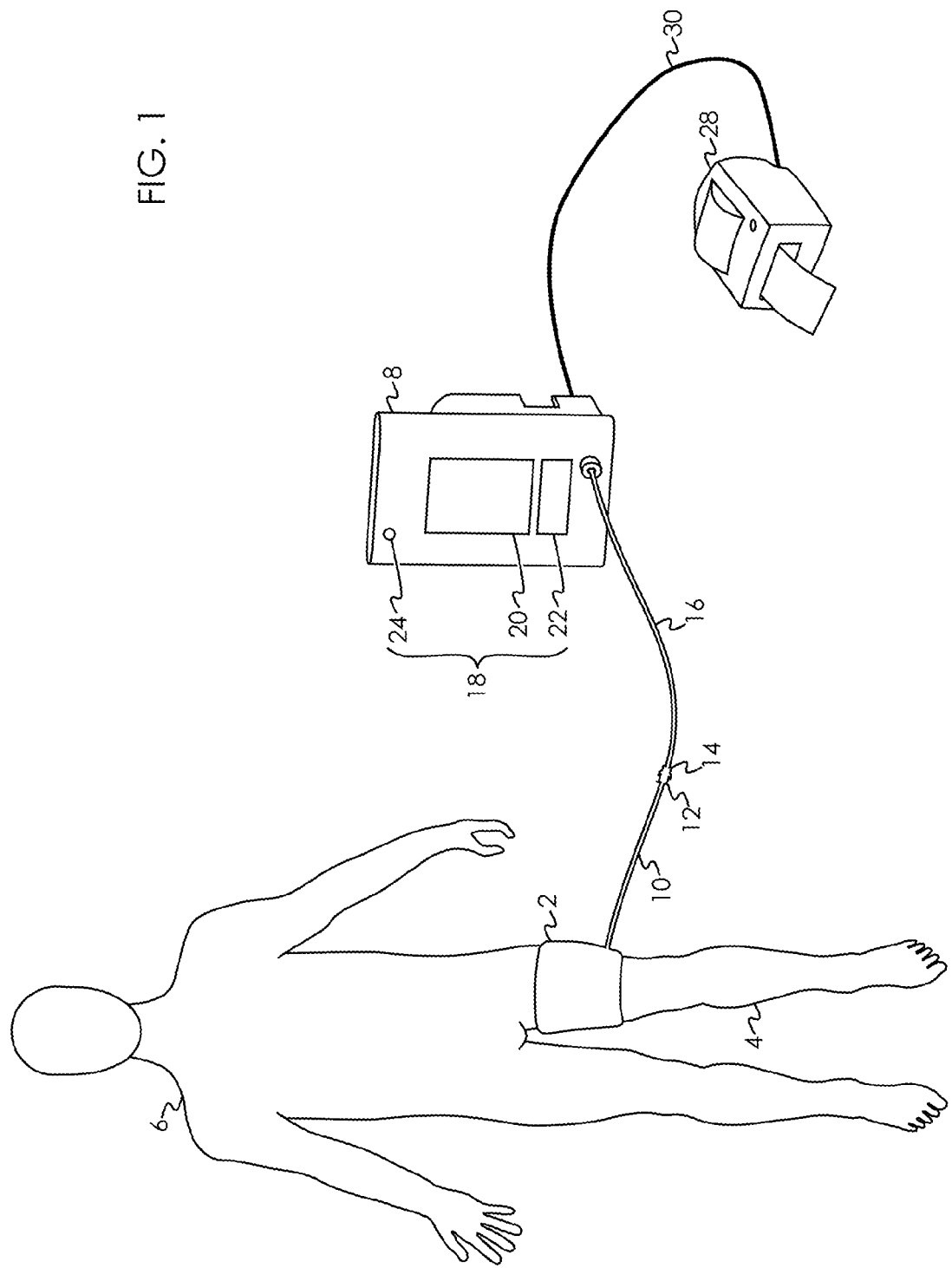
FIG. 1 is a pictorial representation of the preferred embodiment in a surgical application.

FIG. 1 shows an inflatable tourniquet cuff 2 applied to a limb 4 of patient 6 and pneumatically connected to instrument 8. Cuff 2 is supplied with pressurized gas from instrument 8 to occlude the flow of arterial blood in limb 4 past cuff 2. In the preferred embodiment the gas is air, but it will be apparent that other gases or fluids may be used to pressurize cuff 2. A pneumatic passageway to cuff 2 is provided by cuff tubing 10. Cuff tubing 10 is shown to be of sufficient length to allow a pneumatic connection to cuff 2 to be made outside of a sterile surgical field. Cuff tubing 10 is fitted with a male locking connector 12, and mates to form a releasable pneumatic connection with female locking connector 14. Female locking connector 14 is fitted to flexible plastic tubing 16 which connects to instrument 8. Additional connectors may be used to connect tubing 16 to instrument 8 or be otherwise included in the pneumatic passageway between cuff 2 and instrument 8.

Cuff 2 is generally similar in design and construction to the cuffs described by McEwen in U.S. Pat. No. 5,741,295, U.S. Pat. No. 5,649,954, and by Robinette-Lehman in U.S. Pat. No. 4,635,635. Cuff 2 may be formed of plastic coated fabric materials that can withstand, and that can be sterilized by techniques normally used to sterilize medical devices to a level of sterility that allows them to be safely used within a sterile surgical field. Cuff 2 may also be formed of materials that can withstand multiple cleaning and disinfection cycles by techniques normally used to clean and disinfect medical devices which are used during surgical procedures. The pneumatic passageway formed by the inflatable portion of cuff 2, the connections made by connectors 12 and 14, and tubing 16 does not normally permit the escape of gas at the pressures supplied by instrument 8. Accidental damage caused by sharp objects, damage during sterilization or cleaning, wear, and manufacturing defects may cause the leakage of gas from cuff 2, connectors 12 and 14 and tubing 16 when cuff 2 is pressurized.

Instrument 8 includes a user interface 18 that comprises a color graphic display panel 20, a keypad 22, and an alarm indicator 24. A similar user interface, employing a monochromatic graphic display panel has been described in U.S. Pat. No. 5,556,415.

Display panel 20 is employed for the selective display of any of the following information: the level of pressure within cuff 2 as measured by instrument 8 (cuff pressure); desired tourniquet cuff pressure values input by the user; the pressure level to be maintained in cuff 2 when cuff 2 is pressurized (reference pressure level); indicators of potential hazards; pressure warning indicators; alarm reference "limits" or values; alarm messages describing detected alarm events; menus of user selectable commands for the operation of instrument 8; and other information and instructions pertinent to the operation of instrument 8. To facilitate a clear and rapid understanding of the information presented to the user of instrument 8, alphanumeric text, graphic symbols, and color are all used to convey information.

Keypad 22 provides a means for the user of instrument 8 to control the operation of instrument 8. Keypad 22 has an "inflate" key to initiate the pressurization of cuff 2, a "deflate" key to initiate the deflation of cuff 2. Keypad 22 has other keys to permit the user of instrument 8 to input desired tourniquet cuff pressure values, set alarm limits, confirm desired tourniquet cuff pressure values, respond to alarms, and initiate leakage testing of the attached cuff and tubing.

Instrument 8 signals the presence of hazards and alarm conditions via alarm indicator 24 and symbols and text messages describing the alarm condition displayed upon display panel 20. Alarm indicator 24 includes a visual indicator in the form of a red lamp and a speaker for generating audio tones.

It will be appreciated that other types of user interface known in the art may be used by the invention, for example keypad 22 could be replaced by a touch screen interface to display panel 20 allowing the user to interact with instrument 8 by touching selected areas of display panel 20; or the keys of keypad 22 could configured as "soft keys" located adjacent to display; or the user interface could be provided by another remote device in communication with instrument 8.

Instrument 8 maintains a register of events, similar to that described in U.S. Pat. No. 5,911,735, to record events and store the values of relevant parameters at the time of the event such as cuff pressure, reference pressure level, pressure change during cuff leakage testing, inflation time, and alarm thresholds. Events that are recorded and stored by event register 26 shown in FIG. 2 include: the completion of a test for leakage from cuff 2 and the pneumatic passageway between cuff 2 and instrument 8; the pressurization of cuff 2; the deflation of cuff 2; changes made to the reference pressure level; detected alarm conditions, changes made to alarm limits and other events related to the operation of instrument 8.

Event printer 28 is connected to instrument 8 via interface cable 30. Event printer 28 provides a hard copy printout of recorded events and the values of parameters associated with each event as recorded and stored by instrument 8.

In addition to communicating with printer 28, event register 26 also manages communications with an external operating room information network 32. Operating room information network 32 may be either a single device or a collection of devices in communication with instrument 8.

Event register 26 will respond to a request for an event record received from network 32 by transmitting data indicative of any recorded events and the values of parameters associated with each event to network 32 for subsequent remote display along with data collected from other instrumentation in the operating room.

In addition, event register 26 will respond to a request for the value of an operating parameter of instrument 8 received from network 32 by transmitting the current value of the requested operating parameter to network 32. Some parameters for which values may be requested include: cuff pressure; reference pressure level; inflation time; and other parameters indicative of the operational states of instrument 8.

Event register 26 will also respond to a request to change the value of an operating parameter of instrument 8 received from network 32 by attempting to change the value of the operating parameter to the value received from network 32. For example, network 32 may request that the reference pressure level be changed to a new desired tourniquet cuff pressure level.

As described further below event register 26 is inhibited from transmitting values of parameters and inhibited from changing the value of a parameter during certain predetermined operational states of instrument 8. For example, event register 26 is inhibited from transmitting the level of pressure in cuff 2 when testing the magnitude of leakage from cuff 2. This prevents devices in communication with instrument 8 that typically associate pressurization of cuff 2 with the performance of a surgical procedure from misinterpreting the cuff pressure level during a leakage test.

It will be appreciated that instrument 8 may be configured to communicate wirelessly over a radio frequency communication link with printer 28 and operating room information network 32.

Figure 2:
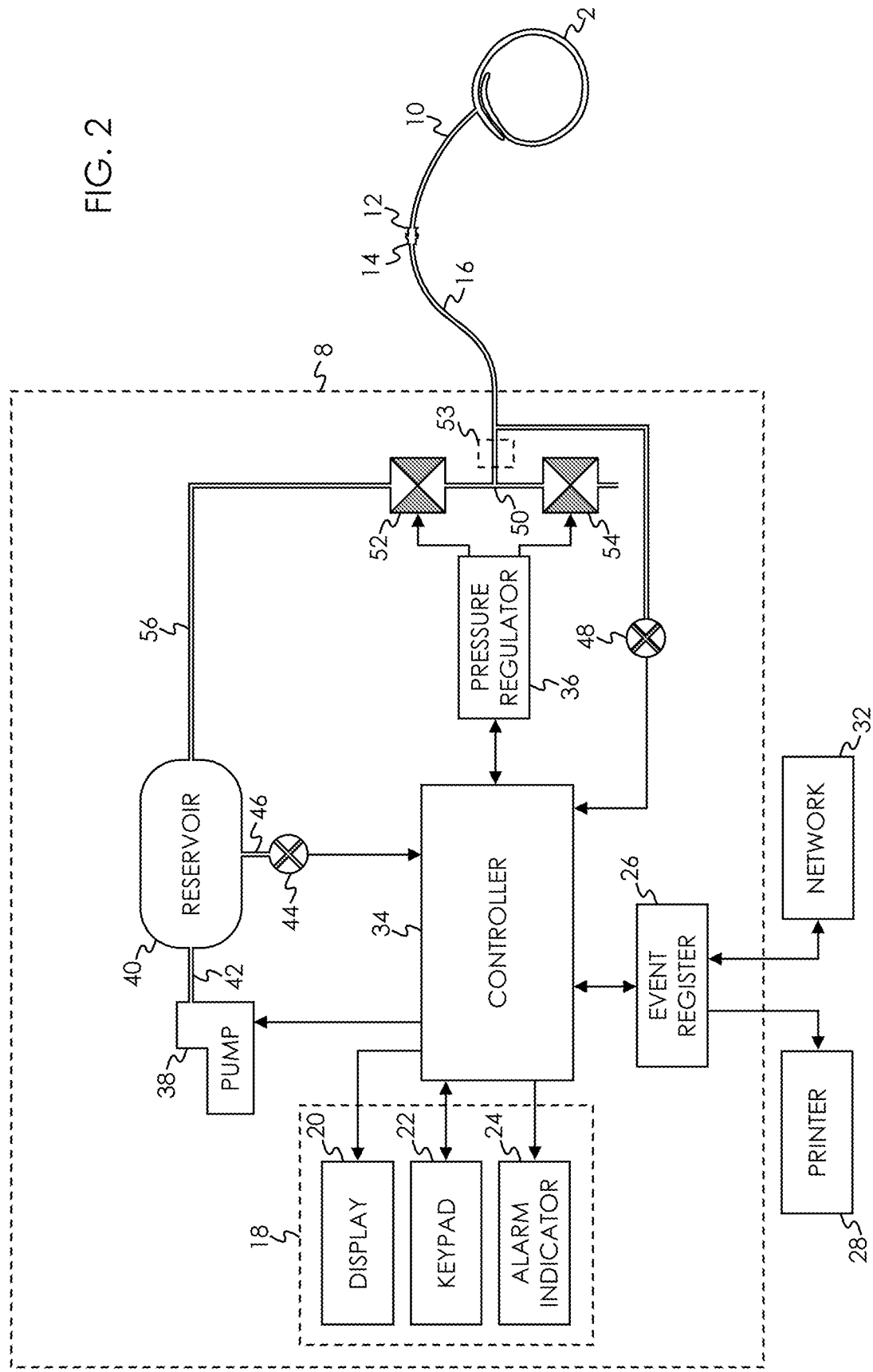
FIG. 2 is a block diagram of the preferred embodiment.

A block diagram of instrument 8 is shown in FIG. 2. Referring FIG. 2, controller 34 is a microcontroller typical of those known in the art with associated memory, analog, and digital peripheral interface circuitry, and other support components. Controller 34 executes software programs that control the operation of instrument 8 as described below. For clarity, and to enable a better understanding of the principles of the invention, some functions that are performed by controller 34 are described and shown in FIG. 2 as separate functional blocks. These function blocks are pressure regulator 36 and event register 26.

A source of pressurized gas for supply to cuff 2 is generated by pneumatic pump 38 which is pneumatically connected to reservoir 40 by tubing 42. In response to control signals from controller 34, pump 38 operates to pressurize reservoir 40. Reservoir pressure transducer 44 is pneumatically connected by tubing 46 to reservoir 40 and generates a signal indicative of the pressure within reservoir 40 which is communicated to controller 34. Controller 34 activates pump 38 to maintain the pressure in reservoir 40 near a predetermined level. It will be appreciated that an external source of pressurized gas for the pressurization of cuff 2 could be provided to instrument 8 eliminating the necessity for pump 38 and reservoir 40.

Controller 34 receives a cuff pressure signal indicative of the pressure within cuff 2 from pressure transducer 48. Pressure transducer 48 is pneumatically connected to cuff 2 via manifold 50 and the pneumatic passageway formed by tubing 16, connectors 12 and 14, and cuff tubing 10. The cuff pressure signal is communicated to pressure regulator 36 by controller 34. As is typical in the art, the pressure within cuff 2 is measured as a gauge pressure (relative to ambient pressure) and expressed in units of mmHg. As shown if FIG. 2, cuff pressure transducer 48 shares a common pneumatic connection to cuff 2 with pressure increase valve 52 and pressure decrease valve 54. Other configurations of pneumatic connection to cuff 2 may be employed. For example, an additional port may be included in cuff 2 for direct connection to transducer 48, or transducer 48 may be incorporated into cuff 2.

When enabled by controller 34, pressure regulator 36 operates to maintain the pressure in cuff 2 (cuff pressure) near the reference pressure level by selectively actuating pressure increase valve 52 and pressure decrease valve 54.

Preferably, the pressure regulator 36 may be disabled by the controller 34 so that the pressure regulator 36 no longer actuates valves 52 and 54 in response to fluctuations in the pressure in cuff 2 and changes in the reference pressure level. The connections among the controller 34, pressure regulator 36 and valves 52, 54 are such that when pressure regulator 36 is disabled, controller 34 may directly actuate valve 52 and 54 in order to pressurize and depressurize cuff 2 for reasons explained more below. Alternatively, the pressure regulator 36 could be effectively disabled by other means, such as diagrammed at dashed block 53 in FIG. 2, which provides for closing the pneumatic passageway to cuff 2 near valves 52 and 54.

Pressure increase valve 52 is an electrically operated normally closed pneumatic valve. The inlet of valve 52 is pneumatically connected via tubing 56 to reservoir 40, the outlet of valve 52 is connected to cuff 2 via the pneumatic passageway formed by manifold 50, tubing 16, connectors 14 and 12, and cuff tubing 10. A pressure increase signal from pressure regulator 36 supplies electrical power for the operation of pressure increase valve 52. When supplied with electrical energy valve 52 opens to allow gas to flow from reservoir 40 to cuff 2, thereby increasing the pressure of gas in the inflatable portion of cuff 2. The amount of electrical power supplied by pressure regulator 36 to valve 52 controls the average rate of gas flow through valve 52. The electrical characteristics of the pressure increase signal are adapted to be appropriate for the operating requirements of valve 52. Valve 52 may be configured as an electrically operated proportional valve wherein the rate of gas flow through valve 52 varies as a function of the electrical current supplied to the valve. Otherwise, valve 52 may be configured as an electrically operated solenoid valve that may be either fully open or fully closed; the average rate of gas flow through the valve may be controlled by pulse width modulating the electrical current supplied to the valve A pneumatic pump may be used in place of pressure increase valve 52 to directly supply gas to increase the pressure in cuff 2 in response to the pressure increase signal from pressure regulator 36.

Pressure decrease valve 54 is also an electrically operated two position normally closed valve similar to valve 52. The inlet of valve 54 is pneumatically connected to cuff 2 via the pneumatic passageway formed by manifold 50, tubing 16, connectors 14 and 12, and cuff tubing 10, the outlet of valve 54 is open to atmosphere. A pressure decrease signal from pressure regulator 36 supplies electrical power for the operation of pressure decrease valve 54. Pressure regulator 36 sets the level of the pressure decrease signal to control the opening of valve 54. Pressure decrease valve 54 responds to the control signal from pressure regulator 36 to allow gas to be vented from cuff 2 to atmosphere, thereby decreasing the pressure of gas in cuff 2.

A proportional integral control algorithm is used by pressure regulator 36 to calculate and set the levels of the pressure increase and pressure decrease control signals for valves 52 and 54 necessary to maintain the cuff pressure near the reference pressure level. It will be appreciated by those skilled in the art that other pressure regulation control algorithms could be employed by pressure regulator 36 to set the levels of pressure increase and pressure decrease control signals for valves 52 and 54.

When enabled, pressure regulator 36 will respond to a difference in pressure between the reference pressure level and the cuff pressure caused by transient volume changes in cuff 2 due to manipulation of limb 4 during surgery or to gas leakage from cuff 2; to add or remove gas from cuff 2 by adjusting the level of the control signals for valve 52 and valve 54 thereby increasing or decreasing the gas pressure within cuff 2 and maintaining the cuff pressure near the reference pressure level.

If during limb manipulation or at other times pressure regulator 36 can not maintain the cuff pressure within the operating limits of pressure regulator 36, controller 34 will indicate a high or low pressure alarm condition to the user via user interface 18 and event register 26 will record a corresponding alarm event. In the preferred embodiment an alarm will be indicated if the pressure regulator 36 cannot maintain the cuff pressure with a predetermined regulation limit of plus or minus 15 mmHg of the reference pressure level. It will be appreciated that other regulation limits may be selected and that they need not be symmetrical around the reference pressure level.

In the preferred embodiment, the reference pressure level may be set to pressure values that are equal to or below a normal safe pressure limit of 475 mmHg. The reference pressure level may also be set to pressure values that are greater than the normal safe pressure limit when additional steps are taken as described below. Controller 34 will not permit the value of the reference pressure level to exceed a predetermined system maximum limit of 600 mmHg and sets the initial value of the reference pressure level to a value that does not exceed the normal safe pressure limit. Values of the reference pressures level that are greater than the normal safe limit and equal to or less than the system maximum limit are extended pressure values.

It will be appreciated that other predetermined pressures may be chosen as safe and system maximum pressure limits and that the limits could be set by the user of instrument 8, set automatically by instrument 8, or set in response to limits received from operating room information network 32 via event register 26.

Setting the reference pressure level to a value greater than the normal safe pressure limit may be necessary in some circumstances to occlude blood flow in limb 4, such as when attempting to occlude blood flow in the limb of a very obese patient. The use of higher cuff pressures such as those above the normal safe pressure limit are associated with higher probabilities injury to limb 4. To reduce the risk of the user increasing the reference pressure level to a pressure value that is above the normal safe limit inadvertently or unintentionally the preferred embodiment has a safe extended pressure interlock. The safe extended pressure interlock sets the value of the reference pressure level. The safe extended pressure interlock produces a hazard indication when a desired tourniquet cuff pressure value exceeds the normal safe limit and requires user confirmation before setting the value of the reference pressure level to a desired tourniquet cuff pressure value that is greater than the normal safe limit.

Figure 3:
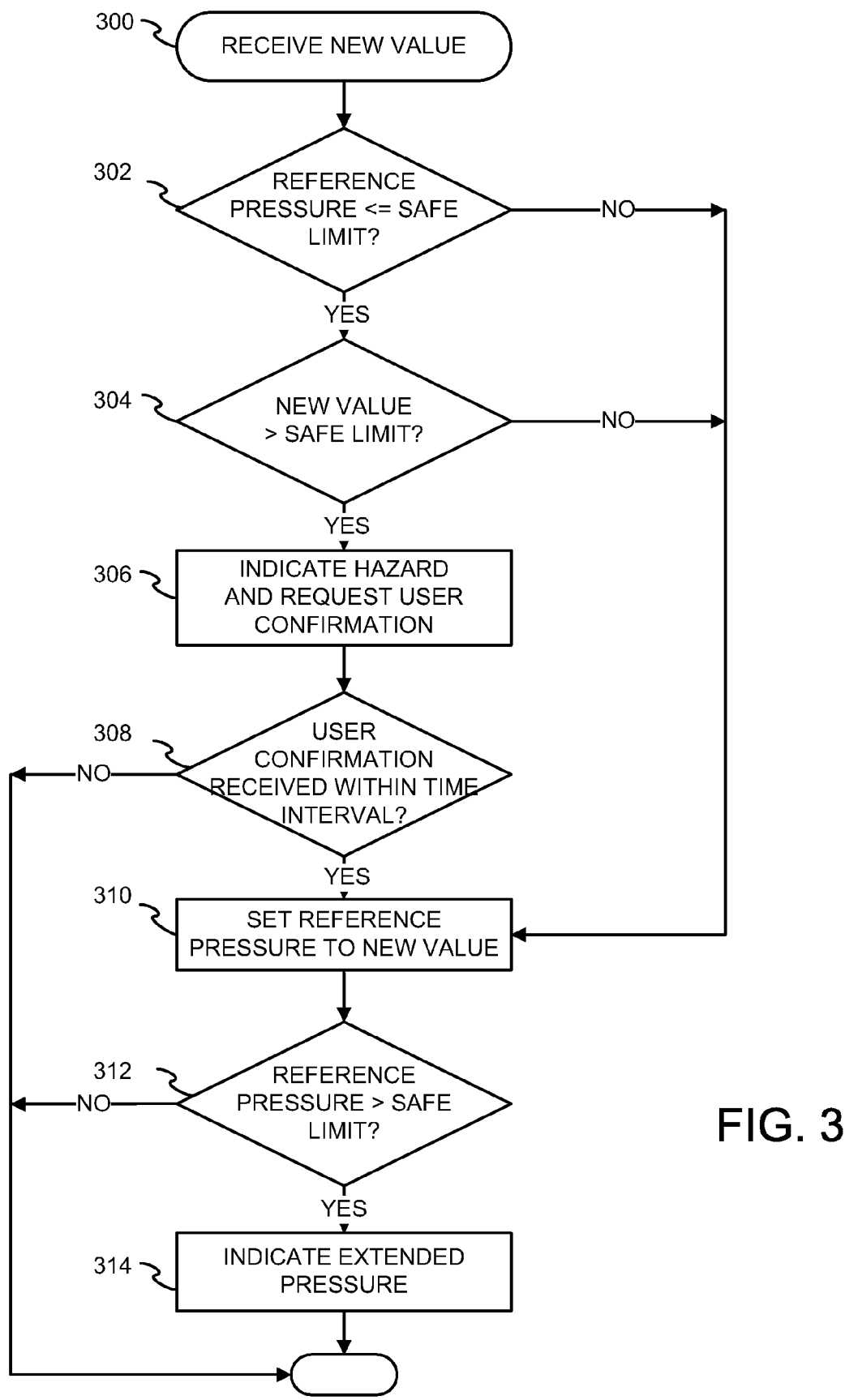
FIG. 3 is a flow chart showing the operation of the safe extended pressure interlock.

A flowchart showing the sequence of operation of the safe extended pressure interlock is shown in FIG. 3. Referring to FIG. 3, the operation of the safe extended pressure interlock begins with an the receipt of a new desired tourniquet cuff pressure value (300), the new desired tourniquet cuff pressure value may be received from user interface 18 in response to the user inputting a value or received from event register in response to a communication from a remote device. If the reference pressure level is equal to or below the normal safe pressure limit (302) and the new desired tourniquet cuff pressure value is greater than the normal safe pressure limit (304); a hazard is indicated by user interface 18 by warning message is shown on display panel 20 and activation of alarm indicator 24 (306). The user is prompted to depress a confirmation key on keypad 22 (308) to permit the reference pressure level to be set to the new desired tourniquet cuff pressure value which is above the normal safe pressure limit. The confirmation key is distinct from the keys used to input the desired tourniquet cuff pressure; if the confirmation key is depressed within a predetermined time interval of 2 seconds (310), the reference pressure level is set to the new desired tourniquet cuff pressure value (312); if the confirmation key is not depressed within the time interval the interlock resets ready to receive a desired tourniquet cuff pressure value and no change is made to the reference pressure level. When the value of the reference pressure level is greater than the normal safe pressure limit an extended pressure warning indicator is shown on display panel 20 (314), to indicate to the user that the reference pressure level has an extended pressure value. The indication that the reference pressure level has an extended pressure value is also communicated by event register 26 to network 32 for possible remote display.

Event register 26 records events related to the operation of the safe extended pressure interlock and communicates parameters related to the operation of the safe extended pressure interlock to printer 28 and network 32. For example, an event is recorded when the new desired tourniquet cuff pressure value is greater than the normal safe pressure limit.

In summary, to increase the value of the reference pressure level to a desired tourniquet cuff pressure value that is greater than the normal safe pressure limit, user confirmation must be received within a predetermined time limit after a hazard warning has been indicated to the user. When the reference pressure level exceeds the normal safe pressure limit, an extended pressure warning is indicated to the user.

The continuous leakage of gas from cuff 2 and the gas passageway between cuff 2 and instrument 8 may prevent pressure regulator 36 from maintaining the cuff pressure near the desired reference pressure level, cause excessive wear of the components comprising instrument 8, and increase the power consumption of the system which will result in a shorter operating time when instrument 8 is powered from a battery supply. Gas leakage may result, for example, from wear or damage to the inflatable portion of cuff 2, needle or towel clip punctures, wear or damage to the sealing surfaces of connectors 12 and 14 and damage to tubing 16.

During periods when cuff 2 is not pressurized to occlude blood flow in limb 4 for the performance of a surgical procedure, the preferred embodiment allows the user to perform a leakage test to conveniently estimate the magnitude of pneumatic leakage from cuff 2 and the pneumatic passageway between cuff 2 and instrument 8. The leakage test rapidly estimates the magnitude of gas leakage from cuff 2, cuff tubing 10 connectors 12 and 14, and tubing 16.

During the leakage test, controller 34 completes a sequence of operations described further below and shown in FIG. 4 to pressurize and depressurize cuff 2 and the pneumatic passageway between cuff 2 and instrument 8. To prevent the inadvertent or unintentional initiation of a leakage test at time when cuff 2 is pressurized for a surgical procedure, user interface 18 is configured to only permit the initiation of a leakage test when the pressure level in cuff 2 and the pneumatic passageway between cuff 2 and instrument 8 is estimated to be near zero. The pressure level in cuff 2 and the pneumatic passageway between cuff 2 and instrument 8 may be estimated by the pressure level sensed by cuff pressure transducer 48 or by the value of the reference pressure level. Only when cuff 2 is fully depressurized can a leakage test be initiated by the user of instrument 8. This protection mechanism prevents the user from initiating a leakage test when cuff 2 is pressurized to occlude blood flow in limb 4 of patient 2, as the sequence of operations preformed during a leakage test would be potentially hazardous to patient 2.

Figure 4:
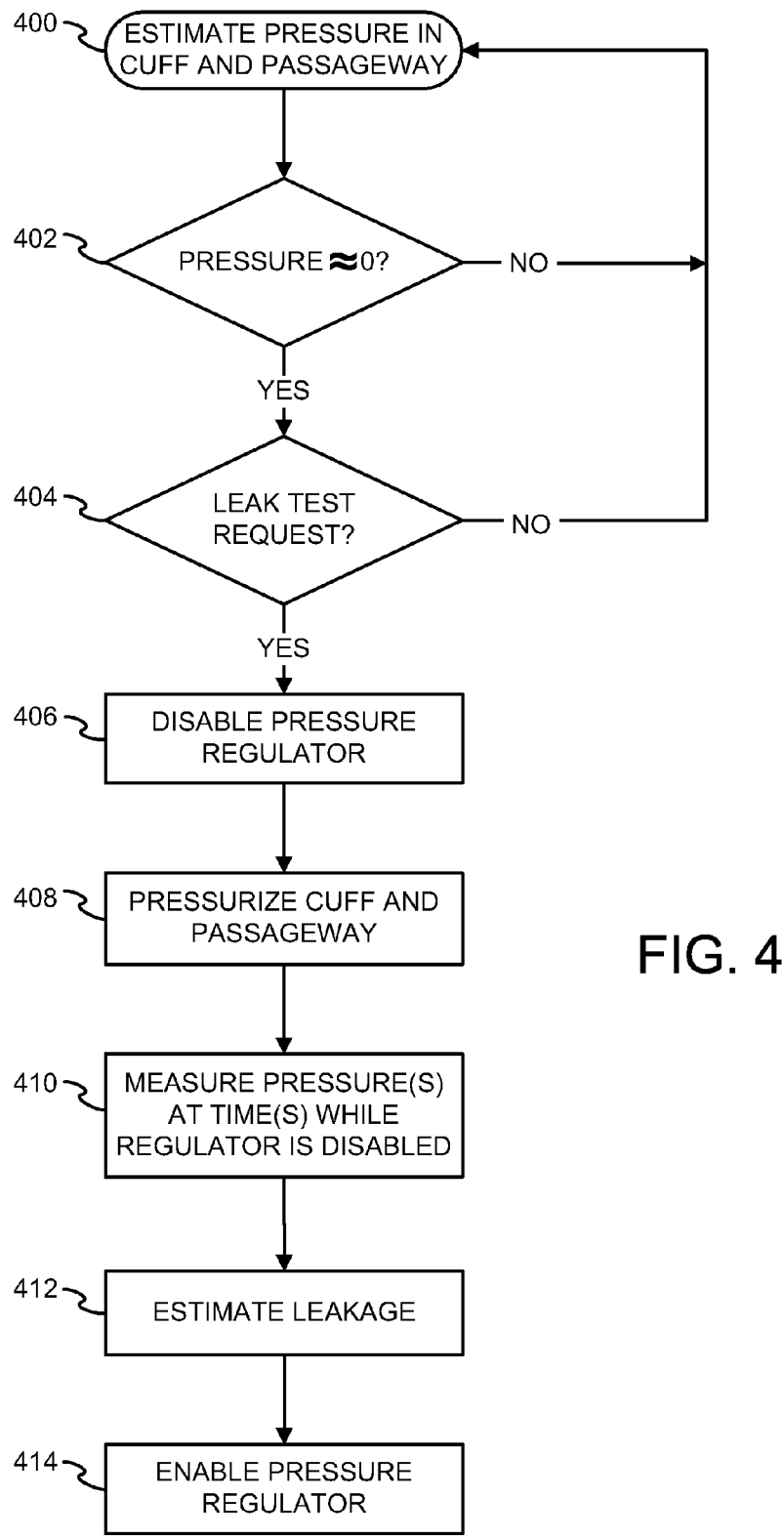
FIG. 4 is a flow chart showing the sequence of operation of the leakage test.

The sequence of operations carried out by controller 34 to in performing a leakage test is shown FIG. 4. Referring to FIG. 4, the pressure level in cuff 2 and the pneumatic passageway between cuff 2 and instrument 8 is estimated (400). If the estimated pressure level in cuff 2 and the pneumatic passageway between cuff 2 and instrument 8 is near zero (402) user interface 18 is configured to enable the user to initiate the performance of a leakage test. In the preferred embodiment a menu selection for the leakage test is made visible on display panel 20 and selectable via keypad 22. It will be appreciated that other methods appropriate for a chosen type of user interface could be used to enable the initiation of a leakage test such as enabling or disabling a the operation of dedicated leakage test key or other enabling or disabling menu choices on a touch screen.

If a request to initiate a leakage test is received (404), controller 34 disables pressure regulator 36 (406) in the preferred a manner as described above. This ensures that pressure regulator 36 does not act to modify the pressure level within cuff 2 and the passageway during the period of time that the leakage test is being performed. Event register 26 is inhibited from transmitting the value of the pressure level within cuff 2 during this operational state when pressure regulator 36 is disabled. Controller 34 then pressurizes cuff 2 and the pneumatic passageway between cuff 2 and instrument 8 (408) by actuating pressure increase valve 52 until the pressure sensed by pressure transducer 48 is near a test pressure level of 250 mmHg. Alternatively, the controller first pressurizes cuff and passageway until the pressure sensed by the pressure transducer is near the test pressure level, and then effectively disables the pressure regulator by closing the pneumatic passageway to cuff 2 near valves 52 and 54, as also described above.

Controller 34 then records the level of pressure within cuff 2 and the pneumatic passageway as sensed by pressure transducer 48. This first pressure level is maintained in the memory of controller 34. After a leakage test period of 30 seconds has elapsed controller 34 again determines the level of pressure within cuff 2 and the pneumatic passageway as sensed by pressure transducer 48 (410). This second pressure level is maintained in the memory of controller 34. Controller 34 next estimates the magnitude of leakage of gas from cuff 2 and the passageway as predetermined function of the first and second pressure levels (412). In the preferred embodiment, the predetermined function evaluates the magnitude of difference between the first and second pressure levels. The estimated magnitude of leakage is indicated to the user via user interface 18. Pressure regulator 36 is enabled and the leakage test is completed (414). After an estimation of the magnitude of leakage has been completed and prior to enabling pressure regulator 36, controller 34 may act to deflate cuff 2 by actuating pressure decrease valve 54.

If the estimated magnitude of leakage exceeds a predetermined magnitude, an alarm indication is produced by user interface 18.

The estimate of the magnitude of leakage (412) may be made any time after the second pressure level stored in the memory of controller 34, and need not immediately precede the step of enabling the pressure regulator (414) as described above.

To obtain a more accurate estimation of the magnitude of leakage from cuff 2 and passageway, controller 34 can, at multiple predetermined intervals during the leakage test period, determine and store the pressure level within cuff 2 and passageway.

For clarity, predetermined values have been used in the description above for the test pressure level and estimation time interval. The estimation time interval need not be predetermined and could be dependent upon a predetermined magnitude of difference between the first and second test pressure levels. Also, values for test pressure level and estimation time interval could set by a user of instrument 8 via user interface 18 or set automatically by instrument 8 dependent upon certain characteristics of the cuff to be tested.

It will be apparent that an estimate of the magnitude gas leakage from cuff 2 could also be made from pressure changes caused by gas leaking into cuff 2 and the passageway if they are initially pressurized to a negative pressure (below atmospheric) by using alternate apparatus to that described above.

An event associated with the completion of a leakage test is stored by event register 26 along with the levels of parameters associated with the test including first and second test pressures, test time interval, and estimated magnitude of leakage. When requested, event register 26 communicates with printer 28 to provide a hardcopy print out of the test results and with network 32 to permit test results to be stored and displayed elsewhere.

We claim:

1. An integrated tourniquet system, comprising:
   an inflatable tourniquet cuff releasably connectable through a connector and tubing to a tourniquet pressure regulator, thereby establishing a gas passageway between the inflatable tourniquet cuff and the tourniquet pressure regulator;
   pressure sensing means for producing an indication of a level of pressure in the inflatable tourniquet cuff and gas passageway;
   user interface means for permitting a user to separately input a request to inflate the cuff and a request for initiation of a leakage test;
   wherein the tourniquet pressure regulator operates to regulate the level of pressure in the inflatable tourniquet cuff and gas passageway near a reference pressure level over a surgical time period suitably long for the performance of a surgical procedure;
   test means responsive to the request for initiation of the leakage test for disabling the operation of the tourniquet pressure regulator for a test period sufficient to perform a test to estimate a magnitude of leakage from the inflatable tourniquet cuff and gas passageway, and for enabling the operation of the tourniquet pressure regulator at the end of the test period, and for inhibiting the performance of the leakage test if the indication of the level of pressure is substantially different from zero at the time of the user request.

2. The apparatus as defined in claim 1 wherein the test means performs the leakage test by inflating the inflatable tourniquet cuff and gas passageway to a first level of pressure at a first test time and estimating a magnitude of leakage of gas from the inflatable tourniquet cuff and gas passageway as a predetermined function of the first level of pressure and a second level of pressure sensed in the inflatable tourniquet cuff and gas passageway at a second test time within the test period.

3. The apparatus as defined in claim 2 wherein the predetermined function evaluates the magnitude of the difference between the first level and the second level.

4. The apparatus as defined in claim 2 wherein the interval between the first test time and the second test time is predetermined.

5. The apparatus as defined in claim 2 wherein the magnitude of the difference between the first test pressure level and the second test pressure level is predetermined.

6. The apparatus as defined in claim 2 and including communication means for communicating the estimate of the magnitude of leakage to remote apparatus.

7. The apparatus as defined in claim 1 wherein the operation of the tourniquet pressure regulator is controlled by at least one electrical signal and wherein the test means disables the operation of the tourniquet pressure regulator by inhibiting the electrical signal.

8. The apparatus as defined in claim 1 wherein the test means disables the operation of the tourniquet pressure regulator by closing the gas passageway near the tourniquet pressure regulator.

9. The apparatus as defined in claim 1 wherein the test means further stores a value indicative of the estimate of the magnitude of leakage, and wherein the apparatus further includes communication means for communicating the stored value to a location remote from the apparatus and for presentation of the stored value in a form perceptible by a user.

10. An integrated tourniquet system, comprising:
    an inflatable tourniquet cuff releasably connectable through a connector and tubing to a tourniquet pressure regulator, thereby establishing a gas passageway between the inflatable tourniquet cuff and the tourniquet pressure regulator;
    the tourniquet pressure regulator being operable for regulating the level of sensed pressure in the inflatable tourniquet cuff near a reference pressure level over a surgical time period suitably long for the performance of a surgical procedure;
    user interface means for permitting a user to separately input a request to inflate the cuff and a request for initiation of a leakage test;
    test means responsive to initiation of the leakage test and operable to disable the tourniquet pressure regulator for a test period during which the cuff is tested for leakage and for enabling the operation of the tourniquet pressure regulator at the end of the test period, and further operable for estimating a magnitude of leakage of gas from the inflatable tourniquet cuff and gas passageway.

11. The apparatus as defined in claim 10 further comprising pressure estimation means for producing an estimate of a level of pressure in the inflatable tourniquet cuff and wherein the test means is further responsive to the estimated level of pressure and wherein the test means is further operable for inhibiting the test if the estimated level of pressure is greater than zero at a time of the request.

12. A method of testing leakage from a tourniquet cuff and gas passageway connecting the tourniquet cuff to a pressure regulator, comprising the steps of:
   estimating a level of pressure in a tourniquet cuff and connected gas passageway;
   enabling a user to separately generate requests for inflating the tourniquet cuff and for a leakage test
   determining the estimated level of pressure at the time the user generates a request for the leakage test;
   inhibiting performance of the leakage test in instances where the estimated level of pressure in the tourniquet cuff is substantially different from zero;
   performing the leakage test if the estimated level of pressure in the tourniquet cuff is near zero by disabling regulation of pressure in the tourniquet cuff for a leakage test period and,
   pressurizing the tourniquet cuff and gas passageway during the leakage test period to a first test level of pressure at a first time, measuring a second test level of pressure at a second time occurring after the first time and
   estimating leakage as a function of the magnitude of the difference between the first test level and the second test level.

13. The method of claim 12 and including the step of enabling a user to generate a request to initiate the performance of the leakage test only at times when the estimated level of pressure is near zero.

14. The method of claim 12, including the step of deflating the tourniquet cuff after the second time and further including the step of thereafter enabling the regulation of the pressure in the tourniquet cuff.

15. The method of claim 12 and including the steps of estimating the magnitude of leakage and producing a human-perceptible indication if the magnitude of leakage is greater than a predetermined magnitude.

16. The method of claim 12 wherein pressurizing step includes the substep of measuring a plurality of additional test levels of pressure at a plurality of additional times occurring between the first time and the second time, and wherein the estimating step includes estimating leakage as a predetermined function of the first and second test levels of pressure at the first and second times respectively and of the plurality of additional test levels at the plurality of additional times.

17. The method of claim 12 wherein the step of enabling the user to generate requests for the leakage test is facilitated by means of a user interface, and wherein the step of disabling the pressure regulation further includes providing a user-perceptible indication while the operation is disabled.

18. A method for testing for leakage from a tourniquet cuff and gas passageway connecting the tourniquet cuff to a pressure regulator, comprising the steps of:
   estimating a level of pressure in the tourniquet cuff and connected gas passageway;
   if the estimated level of pressure is substantially different from zero, preventing user initiation of a leakage test;
   if the estimated level of pressure is near zero, enabling initiation of the leakage test by disabling regulation of pressure in the tourniquet cuff;
   if the leakage test is initiated, pressurizing the tourniquet cuff and gas passageway to a first level of pressure near a first time, measuring a second level of pressure at a second time after the first time wherein during the period between the first time and the second time and the pressurizing is halted and during which a pressure regulator normally operable for maintaining a level of pressure in the tourniquet cuff and connected gas passageway near a reference pressure level is disabled, and determining a magnitude of difference between the first and second levels of pressure and producing an indication of leakage as a predetermined function of the magnitude.

19. The method of claim 18 and including the step of deflating the tourniquet cuff after the second time.

20. The method of claim 18 and including the step of enabling the operation of the pressure regulating means after the second time.

21. The method of claim 18 wherein the first level of pressure is predetermined and wherein the second time is predetermined.

* * * * *